United States Patent [19]

Sharpe

[11] 3,982,538
[45] Sept. 28, 1976

[54] SAFETY VALVES FOR PROTECTION AGAINST LIQUID CONTAMINATION

[75] Inventor: Anthony Nelson Sharpe, Aylmer, Canada

[73] Assignee: N.V. Internationale Octrooi Maatschappij"Octropa", Rotterdam, Netherlands

[22] Filed: July 8, 1974

[21] Appl. No.: 486,298

[30] Foreign Application Priority Data
July 9, 1973    United Kingdom............... 32526/73

[52] U.S. Cl............................... 128/276; 137/197; 73/425.4 P
[51] Int. Cl.².......................................... A61M 1/00
[58] Field of Search .......... 128/233, 276, 277, 278, 128/350 V; 261/4–7; 141/26, 286; 137/197–199, 251, 806; 73/425.4 P; 131/10.1

[56] References Cited
UNITED STATES PATENTS

| | | | |
|---|---|---|---|
| 2,348,831 | 5/1944 | Mathis | 73/425.4 P |
| 2,850,033 | 9/1958 | Hartle | 137/197 |
| 3,285,296 | 11/1966 | Ishimaro et al. | 141/26 |
| 3,719,197 | 3/1973 | Pannier, Jr. et al. | 128/276 |

*Primary Examiner*—Robert W. Michell
*Assistant Examiner*—Henry S. Layton
*Attorney, Agent, or Firm*—Kaufman & Kramer

[57] ABSTRACT

A safety valve which may be used in a pipette or in medical or biological equipment such as collection bottles, employs a carrier which is inserted in a flow line and contains a material which swells in the presence of an unwanted fluid to block the line and provide protection against contamination.

2 Claims, 8 Drawing Figures

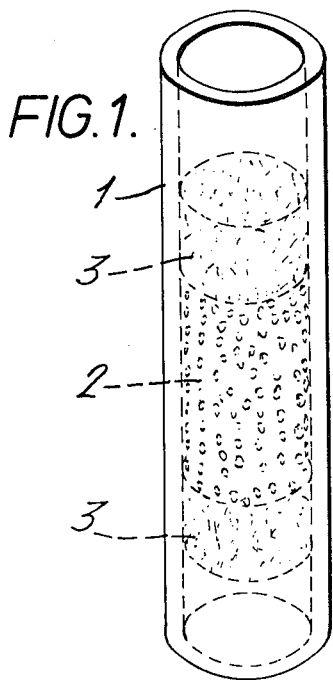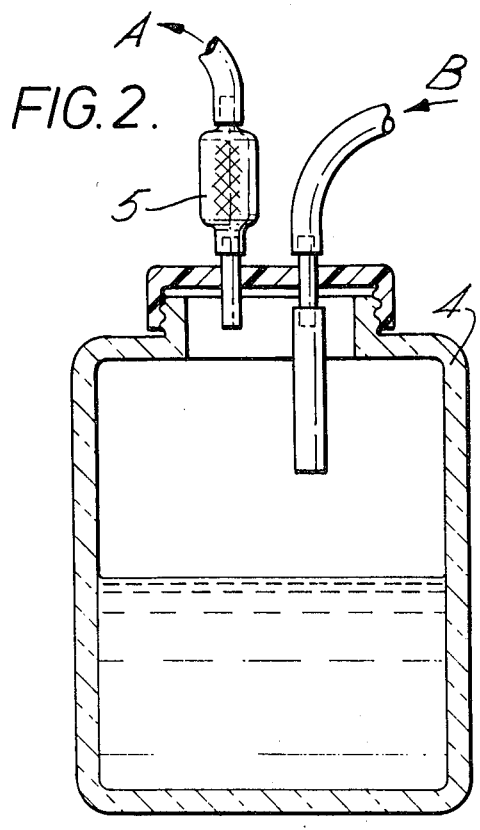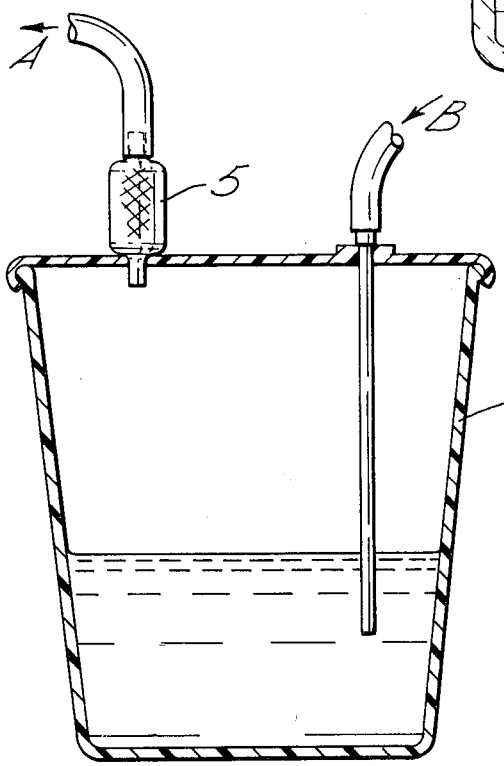

SAFETY VALVES FOR PROTECTION AGAINST LIQUID CONTAMINATION

This invention relates to safety valves for protection against fluid contamination particularly in chemical, biological and bacteriological equipment and instrumentation and to apparatus incorporating such valves. One specific use for these safety valves is in surgical collection bottles, and another is in pipettes.

Where bacteriological samples are to be dispensed it is important that traces of the sample do not reach and cause contamination in areas where they are not wanted. For example it is vital that with manual pipetting, traces of a toxic sample are not sucked up into the mouth; and in mechanical devices it is important that pumping and feeding mechanisms are not contaminated in use. Where mechanisms are contaminated there is risk of traces of one sample being carried over to the next, and the need for very thorough cleaning between each operation. With medical equipment, such as surgical collection bottles for body fluid, the possibility of infected liquid being carried into mechanical parts and giving rise to further infection is something to be avoided; and in equipment used in food production bacteriological hazards should not be allowed to arise. The invention is concerned with safeguarding against such problems.

Accordingly the invention provides a safety valve consisting of a hollow carrier arranged for insertion in a flow line and containing a material which allows flow through said carrier of one form of fluid, but which in the presence of a second form of fluid swells to block said carrier and prevent further flow.

In its simplest form the material is arranged so as to allow air or other gases to flow through, but in the presence of a liquid, the material absorbs that liquid, swells and blocks the carrier.

The invention finds particular application in surgical collection bottles for body fluid, where it can replace the conventional ball float valve resulting in a cheaper, and in some cases disposable, device.

The material may be a packing of granular or powdered water-soluble polymeric material, for example gelatine, sodium alginate or agar, which allows passage of air (even when the air is damp). If liquid water enters the device, however, the polymer immediately swells and blocks the carrier, after which neither water nor air can pass.

Certain chemically modified cellulose derivatives in granular form are particularly effective as the material in the carrier which swells in the presence of water. A particular example is the British Celanese product Courlose p.350 which is powdered or granular form of purified sodium carboxymethyl cellulose (a 1% solution has a viscosity of 300 to 450 cps). Starch derivatives may also be used.

The device may also be used when both fluids are liquids. For example if the material in the carrier is in the form of hydrocarbon polymer granules, e.g. rubber, a flowing stream of water will be stopped by the presence of a hydrocarbon liquid in that stream. By selection of a different material the converse can be achieved i.e. a flowing stream of hydrocarbon liquid will be stopped when significant traces of water appear.

It will be appreciated that in selecting a material for use in the safety valve according to the invention, only a single clearly recognisable property, namely swelling and blocking in the presence of the unwanted fluid, has to be identified in the material. Thus the material can be selected very easily by trial and error, or through recourse to well-known Chemical textbooks, e.g. Kirk-Othmer Encyclopaedia of Chemical Technology Vol III p. 599 et seq and particularly page 622. It will be understood also, that the arrangement should ensure that the valve does block when required under the normal conditions of use. To ensure this, excessive temperatures, pressures or other conditions of use which might wash or dissolve the material away altogether should not be employed, and in some cases mechanical restraint should be included, for example cottonwool or other inert plugs, or other mechanical constraint which allows flow of the normal fluid but retains the blocking material in place.

Several embodiments of the invention will now be described by way of example with reference to the accompanying diagrammatic drawings in which:

FIG. 1 shows a perspective view of an insert;

FIG. 2 is a sectioned side elevation of a surgical vacuum pump collection bottle;

FIG. 3 is a sectioned side elevation of another form of collection bottle;

Figure 4:
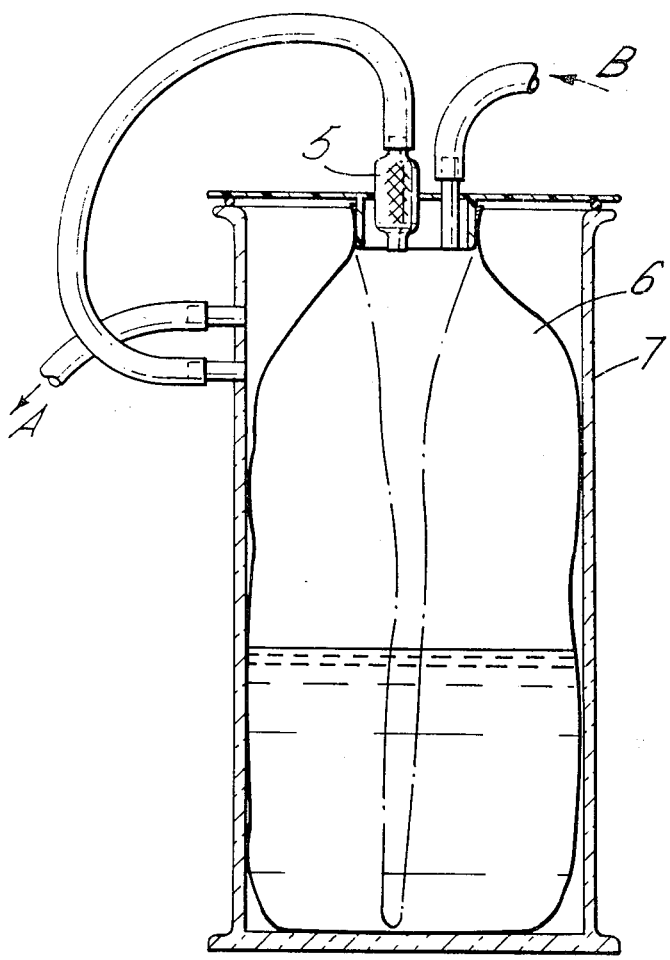
FIG. 4 is a sectioned side elevation of a third form of collection bottle.

Referring to FIG. 1, a safety valve in accordance with the invention comprises a hollow carrier 1 which is in tubular form and therefore capable of insertion in a flow line. The carrier contains a material 2 consisting of loosely packed granular water soluble polymeric material. Suitable materials are gelatine, sodium alginate, and agar for protection of a flowing gas against ingress of liquid. Courlose p.350 made by British Celanese Limited was used in the present example. The granular material is maintained in position by cottonwool plugs 3 at each end. With alternative shapes of carrier the material is kept in place by suitable shaping of the internal walls of the hollow carrier rather than the cottonwood plugs.

The carrier described in FIG. 1 may be used in numerous different applications in foods, medical and similar equipment where fluids flow, to safeguard against accidental contamination. Two such, one for medical collection bottles and the other for pipettes will now be described.

FIG. 2 shows a glass collection bottle 4 for use in conjunction with a surgical vacuum pump in pumping body fluid from a patient after an operation. In use a vacuum pump withdraws air at the location of arrow A while the reduced pressure within the container results in body liquid being withdrawn into the container in the direction of arrow B.

Such vessels are well known and conventionally a float valve near the top of the container acts as a protection device to protect for the situation when the liquid level within the container reaches the top, to ensure that liquid is not then drawn into the vacuum pump along the path of arrow A.

The conventional valve assembly is replaced in accordance with the invention by an insert 5 constructed internally as shown in FIG. 1. This is cheaper and more convenient in use than the conventional float valve mechanism.

In practice, operation of the system will not normally result in operation of the safety valve 5, the operator observing the liquid level and switching off the pump and replacing the bottle when liquid level is near but not quite at the top. When however the liquid level does reach the top of the container and start to flow in the direction of arrow A, it flows into the safety valve 5, causes the granulated gelling material 2 to absorb liquid, swell and block off further flow along the vacuum line. This ensures that no contamination of the vacuum pump takes place and it is then a simple matter to insert a new valve 5 and clean out the bottle for further use. The safety valve is a cheap and easily replaceable item.

FIG. 3 shows a similar system where the container is a plastics bottle. This has become possible since sterilisation and cleaning of the relatively expensive valve mechanism has been eliminated.

FIG. 4 shows a system where the bottle has been replaced by a disposable collapsible bag 6. This disposable bag is suspended within an outer container 7 and the air line system is arranged so that the flexible bottle 6 automatically opens out in use. This is achieved by feeding the outlet of the air line from the insert 5 to the space between the inner container 6 and the outer container 7, and thence to the vacuum pump. Since there is a slight drop in pressure across the insert 5, this means that there is a greater vacuum on the outside of the inner container 6 than on the inside and therefore this causes the container to open out as soon as the vacuum pump is switched on.

Figure 5:
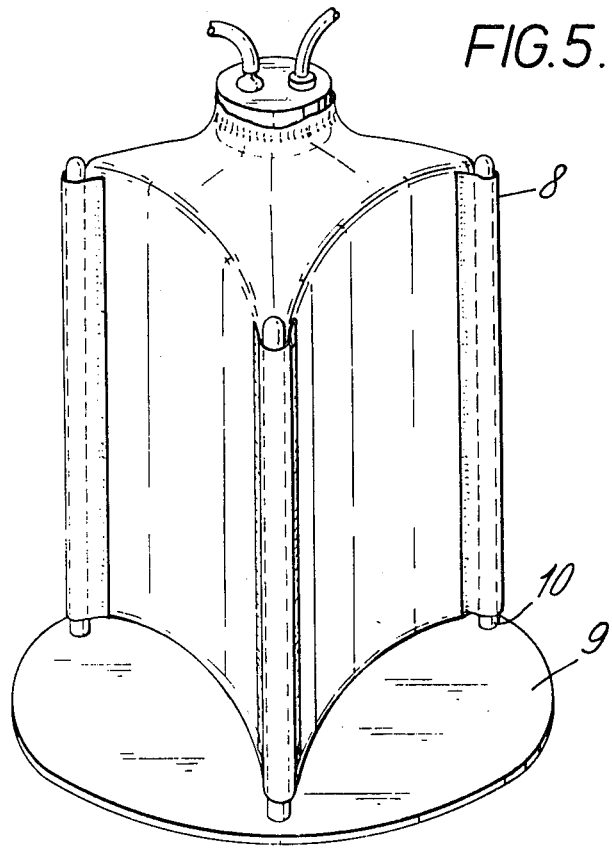
FIG. 5 is a perspective view of a fourth form of collection bottle.

FIG. 5 shows a further form in which the outer container is no longer needed nor are the measures for opening out the bag required. In this case the bag has loops 8 welded at its corners and the bag is looped over a holder 9 having upstanding bars 10 which are inserted into the loops 8. Thus the bag is held open during use.

Figure 6:
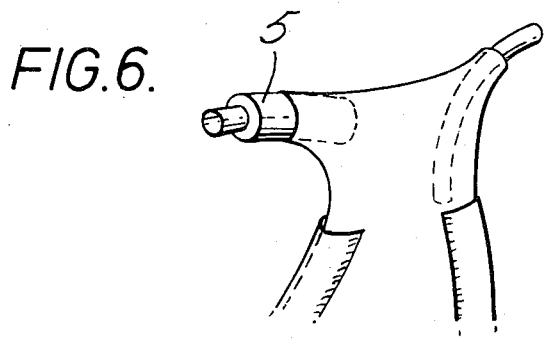
FIG. 6 is a perspective view of a modified part of the FIG. 5 bottle.

In the arrangement shown in FIG. 5 the bag is disposable while a lid including the pipe connections and the valve 5 is a permanent component. FIG. 6 shows a variant on the FIG. 5 arrangement where the connections and the valve 5 are all part of the disposable system.

Figure 8:
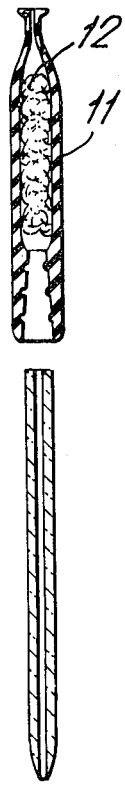
FIG. 7 and FIG. 8 show views of a pipette using an insert.
Figure 7:
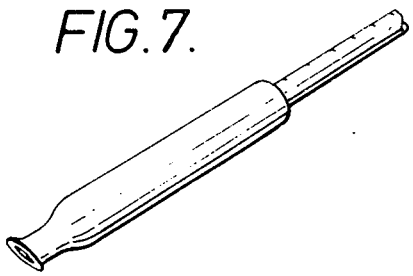

FIGS. 7 and 8 show the valve as applied to a hand pipette. In this case the pipette has a mouth piece 11 which incorporates the valve and the water swellable granules which are located in a hollow part of the mouth piece at the location 12. In operation the mouth piece is simply slipped onto the end of a standard pipette and if the operator sucks liquid up too far it blocks off the pipette and harmful liquids cannot enter the operator's mouth. When the mouth piece is blocked it can either be discarded, or it can be cleaned out and refilled with material in the cavity 12 for further use.

What is claimed is:

1. A safety valve for protection against fluid contamination comprising a hollow carrier adapted for insertion in a flow-line and containing a valve element consisting essentially of a granular or powdered gelling material which allows the flow through said carrier of gas in the absence of water, but which in the presence of water swells to block said carrier and prevent further flow, said gelling material being selected from the group consisting of gelatine, sodium alginate, agar, sodium carboxy methyl cellulose and swellable starch derivatives.

2. A safety valve for protection against fluid contamination comprising a hollow carrier adapted for insertion in a flow-line and containing a valve element consisting essentially of a granular or powdered gelling material which allows the flow through said carrier of water in the absence of hydrocarbon liquid in the water, but which in the presence of hydrocarbon liquids in the water swells to block said carrier and prevent further flow, said gelling material consisting of swellable hydrocarbon polymer granules.

* * * * *